United States Patent [19]

Clough et al.

[11] Patent Number: 5,346,902

[45] Date of Patent: Sep. 13, 1994

[54] FUNGICIDAL DIAZINYL DIOXIME

[75] Inventors: John M. Clough, Marlow; Christopher R. A. Godfrey, Bracknell; Paul J. de Fraine, Wokingham, all of England

[73] Assignee: Imperial Chemical Industries PLC, Millbank, England

[21] Appl. No.: 60,396

[22] Filed: May 11, 1993

Related U.S. Application Data

[62] Division of Ser. No. 745,820, Aug. 16, 1991, Pat. No. 5,238,956.

[30] Foreign Application Priority Data

Aug. 22, 1990 [GB] United Kingdom ............. 9018408.6

[51] Int. Cl.$^5$ ................. A61K 31/505; C07D 239/34; C07D 239/46; C07D 239/42
[52] U.S. Cl. .................. 514/269; 514/241; 514/242; 514/245; 514/247; 514/252; 514/255; 514/256; 514/258; 544/224; 544/239; 544/240; 544/241; 544/243; 544/298; 544/319; 544/321; 544/322; 544/326; 544/327; 544/334; 544/337; 544/353; 544/354; 544/356; 544/357; 544/405; 544/408; 544/409

[58] Field of Search ............... 514/241, 242, 245, 252, 514/255, 256, 258, 269, 311, 312, 314, 336, 344, 345, 349, 352, 365, 369, 370, 372, 383, 384, 438, 445, 447; 544/180, 182, 194, 195, 196, 197, 198, 199, 204, 211, 212, 213, 214, 215, 216, 217, 218, 219, 232, 238, 239, 240, 241, 243, 295, 296, 298, 319, 322, 326, 327, 334, 335, 337, 353, 354, 356, 357, 405, 408, 409; 546/22, 23, 152, 153, 155, 173, 176, 180, 255, 261, 264, 266, 276, 280, 283, 284, 286, 287, 288, 289, 290, 296, 300, 301, 302, 303, 304, 307, 329; 548/146, 182, 183, 184, 186, 189, 190, 191, 193, 197, 198, 206, 213, 214, 255, 262.2, 263.2, 263.4, 263.8, 264.2, 264.4, 264.8, 265.2, 266.6, 266.8, 267.4, 267.8, 268.6; 549/5, 6, 218, 356, 416, 417, 419

[56] References Cited

U.S. PATENT DOCUMENTS

| | | | |
|---|---|---|---|
| 4,829,058 | 5/1989 | Wenderoth et al. | 514/522 |
| 4,999,042 | 3/1991 | Anthony et al. | 71/88 |
| 5,051,447 | 9/1991 | Wenderoth et al. | 514/534 |
| 5,055,471 | 10/1991 | de Fraine et al. | 514/255 |
| 5,194,662 | 3/1993 | Brand et al. | 560/35 |

FOREIGN PATENT DOCUMENTS

| | | |
|---|---|---|
| 460575 | 12/1991 | European Pat. Off. |
| 463488 | 1/1992 | European Pat. Off. |
| 9007493 | 7/1990 | PCT Int'l Appl. |

Primary Examiner—Mukund J. Shah
Assistant Examiner—Y. N. Gupta
Attorney, Agent, or Firm—William E. Dickheiser

[57] ABSTRACT

Fungicidal compounds of the formula (I):

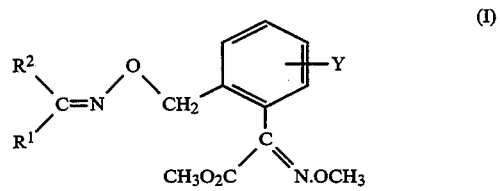

and stereoisomers thereof, wherein Y is a specified small group or single atom and $R^1$ and $R^2$ are selected from a wide range of specified substituents.

10 Claims, No Drawings

FUNGICIDAL DIAZINYL DIOXIME

This is a continuation of application Ser. No. 7/745,820, filed Aug. 16, 1991, now U.S. Pat. No. 5,238,956.

This invention relates to derivatives of propenoic acid useful as fungicides, to processes for preparing them, to compositions containing them, and to methods of using them to combat fungi, especially fungal infections of plants.

According to the present invention there is provided a compound having the formula (I), and stereoisomers thereof, wherein Y is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; and $R^1$ and $R^2$, which may be the same or different, are hydrogen, optionally substituted alkyl, optionally substituted cycloalkyl, optionally substituted heterocyclylalkyl, optionally substituted cycloalkylalkyl, optionally substituted aralkyl, optionally substituted heteroarylalkyl, optionally substituted aryloxyalkyl, optionally substituted heteroaryloxyalkyl, optionally substituted heteroarylthioalkyl, optionally substituted arylthioalkyl, optionally substituted alkenyl, optionally substituted alkynyl, optionally substituted alkoxy, optionally substituted aryl, optionally substituted heteroaryl, optionally substituted aryloxy, optionally substituted heteroaryloxy, nitro, halo, cyano, $-NR^3R^4$, $-CO_2R^3$, $-CONR^3R^4$, $-COR^3$, $-S(O)_nR^3$ wherein n is 0, or 2, $(CH_2)_mPO(OR^3)_2$ wherein m is 0 or 1, or $R^1$ and $R^2$ join to form a carbocyclic or heterocyclic ring system; and $R^3$ and $R^4$, which are the same or different, are hydrogen, optionally substituted alkyl, optionally substituted aralkyl, optionally substituted alkenyl, optionally substituted alkynyl, optionally substituted aryl or optionally substituted heteroaryl, or $R^3$ and $R^4$ join to form an optionally substituted heterocyclic ring.

The compounds of the invention contain at least two carbon-nitrogen double bonds and are sometimes obtained in the form of mixtures of geometric isomers. However these mixtures can be separated into individual isomers and this invention embraces such isomers and mixtures thereof in all proportions.

The individual isomers which result from the unsymmetrically substituted double bond of the oxime ether groups are identified by the commonly used terms "E" and "Z". These terms are defined according to the Cahn-Ingold-Prelog system which is fully described in the literature (see, for example, J March, "Advanced Organic Chemistry", 3rd edition. Wiley-Interscience, page 109 et seq).

For the carbon-nitrogen double bond of the oximinoacetate group, usually one isomer is more active fungicidally than the other, the more active isomer usually being the one wherein the groups $-CO_2CH_3$ and $-OCH_3$ are on opposite sides of the carbon-nitrogen double bond (the (E)-isomer). These (E)-isomers form a preferred embodiment of this invention.

The use hereinafter of the formula (A) signifies a separable mixture of both geometric isomers about the carbon-nitrogen double bond of the oxime ether, i.e. the isomers containing the groups of formulae (B) and (C).

Geometric pairs of isomers about the carbon-nitrogen bond of the oximino-acetate group of the compounds listed later in Table I are identified by the letters A and B. In many instances, using solvent systems such as ether or ethyl acetate, or mixtures of one of these with hexane, the isomers termed A and B of a compound have significantly different Rf values when analysed by thin-layer chromatography on silica gel. Of each pair of isomers the isomer which is the less polar on silica gel is termed the Isomer A and the more polar one, Isomer B.

Halo includes fluoro, chloro, bromo and iodo.

Alkyl and the alkyl moieties of alkoxy, aralkyl, aryloxyalkyl, heteroarylalkyl, heteroaryloxyalkyl, arylthioalkyl, heteroarylthioalkyl, can be in the form of straight or branched chains and, unless otherwise stated, suitably contain from 1 to 6 carbon atoms. Examples are methyl, ethyl, iso-propyl and tert-butyl. Optional substituents include halo (especially chloro and fluoro), hydroxy and $C_{1-4}$ alkoxy. Examples of substituted alkyl and substituted alkoxy are trifluoromethyl and trifluoromethoxy.

Cycloalkyl is suitably $C_{3-6}$ cycloalkyl, for example cyclopropyl or cyclohexyl, and cycloalkylalkyl is suitably $C_{3-6}$ cycloalkyl($C_{1-4}$)alkyl, for example 1- or 2-cyclopropylethyl.

Alkenyl and alkynyl suitably contain from 2 to 6 carbon atoms, typically 2 to 4 carbon atoms, in the form of straight or branched chains. Examples are ethenyl, allyl and propargyl. Substituted alkenyl and alkynyl groups include optionally substituted aryl- and heteroarylalkenyl (especially optionally substituted aryl- and heteroaryl($C_{2-4}$)alkenyl and, particularly, optionally substituted phenylethenyl) and aryl- and heteroarylalkynyl.

Aryl and the aryl moieties of aralkyl, arylalkenyl, arylalkynyl, aryloxy and aryloxyalkyl include phenyl and naphthyl.

The carbocyclic or heterocyclic ring system which $R^1$ and $R^2$ may form together is suitably a $C_{4-10}$ (typically $C_{5-10}$) aliphatic, aromatic or mixed aliphatic/aromatic carbocyclic ring system, for example cyclopentyl, cyclohexyl, cyclohexadienonyl and such groups carrying one or two optionally substituted fused benzene rings and/or substituents such as methyl; or it may be a 4- to 10-membered heterocyclic ring system, for example tetrahydropyranyl.

The term heteroaryl is used to described aromatic heterocyclic groups. Heteroaryl and heterocyclyl and the heteroaryl and heterocyclyl moieties of other groups, such as heteroaryloxyalkyl and heterocyclylalkyl, are typically 5- or 6-membered rings containing one or more O, N or S heteroatoms which may be fused to one or more other aromatic, heteroaromatic or heterocyclic rings such as a benzene ring. Examples are thienyl, furyl, pyrrolyl, isoxazolyl, oxazolyl, pyrazolyl, imidazolyl, triazolyl, thiazolyl, pyridyl, pyrimidinyl, pyrazinyl, pyridazinyl, triazinyl, benzofuryl, benzothienyl, dibenzofuryl, indolyl, quinolinyl and quinoxalinyl groups and, where appropriate, N-oxides and N-alkyl salts thereof.

The optionally substituted heterocyclic ring which $R^3$ and $R^4$ may join together to form is suitably a 5 to 7 membered hetero ring having 1 to 3 heteroatoms which are independently selected from O, S or N, and having 1 to 3 substituents which are, for example, halogen, cyano, nitro, $C_{1-6}$ alkyl, $C_{1-6}$ alkoxy, group, $C_{1-6}$ alkylthio, or a heterocyclic ring such as described in the previous paragraph. Examples are pyrrolidine, piperidine. morpholine, thiomorpholine, piperazine, hexamethyleneimine, tetrahydroquinoline, tetrahydroisoquinoline and 2,3-dihydro-1,4-benzoxazine.

Substitutents which may be present in optionally substituted aryl and heteroaryl moieties include one or more of the following: halo, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$alkylthio (especially methylthio), hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted aryl($C_{1-4}$)alkyl (especially optionally substituted benzyl, optionally substituted phenethyl and optionally substituted phenyl-n-propyl) in which the alkyl moiety is optionally substituted with hydroxy, optionally substituted heteroaryl($C_{1-4}$)alkyl (especially optionally substituted pyridyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy), optionally substituted heteroaryl($C_{1-4}$)alkoxy (especially optionally substituted pyridyl- or pyrimidinyl($C_{1-4}$)alkoxy), optionally substituted aryloxy($C_{1-4}$)alkyl (especially phenoxymethyl), optionally substituted heteroaryloxy($C_{1-4}$)alkyl (especially optionally substituted pyridyloxy- or pyrimidinyloxy($C_{1-4}$)alkyl), acyloxy, including $C_{1-4}$ alkanoyloxy (especially acetyloxy) and benzoyloxy, cyano, thiocyanato, nitro, —NR′R″, —NHCOR′, —NHCONR′R″, —CONR′R″, —COOR′, —OSO$_2$R′, —SO$_2$R′, —COR′, —CR′=NR or —N=CR′R″ in which R′ and R″ are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR′R″, —NHCOR′, —NHCONR′R″, —CONR′R″, —COOR′, —SO$_2$R′, —OSO$_2$R′, —COR′, —CR′=NR″ or —N=CR′R″ in which R′ and R″ have the meanings given above.

In one aspect the invention includes a compound of formula (I) wherein Y is hydrogen, halo, hydroxy, methyl, methoxy, trifluoromethyl, trifluoro-methoxy, $C_{1-2}$ alkylcarbonyl, $C_{1-2}$ alkoxycarbonyl, phenoxy, nitro or cyano; $R^1$ is $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, cyano, phenyl($C_{1-4}$)alkyl, phenyl, a 5- or 6-membered aromatic heterocycle containing one or more O, N or S atoms optionally fused to a benzene ring, the aromatic or heteroaromatic moieties of any of the foregoing being optionally substituted with one or more of halo, hydroxy, $C_{1-4}$ alkyl, halo($C_{1-4}$)alkyl, $C_{1-4}$ alkoxy, halo($C_{1-4}$)alkoxy, $C_{1-4}$ alkylcarbonyl, $C_{1-4}$ alkoxycarbonyl, nitro, cyano, phenyl, phenoxy, benzyl or benzyloxy; and $R^2$ is hydrogen, halo, $C_{1-4}$ alkyl, halo($C_{1-4}$)alkyl, $C_{1-4}$ alkylcarbonyl, $C_{1-4}$ alkoxycarbonyl, cyano or phenyl; or $R^1$ and $R^2$ join together to form a $C_{5-10}$ carbocyclic ring system.

In another aspect the invention includes a compound of formula (I) wherein Y is hydrogen or halo; $R^1$ is $C_{1-4}$ alkyl, benzyl, $C_{1-4}$ alkylcarbonyl, $C_{1-4}$ alkoxycarbonyl, cyano, phenyl, thienyl, triazolyl, thiazolyl, pyridyl, pyrimidinyl, pyrazinyl, pyridazinyl, triazinyl, quinolinyl or quinoxalinyl, the aromatic or heteroaromatic moieties of any of the foregoing being optionally substituted with one or more of halo, $C_{1-4}$ alkyl, trifluoromethyl, $C_{1-4}$ alkoxy, trifluoromethoxy, nitro, cyano, phenyl or benzyloxy; and $R^2$ is hydrogen, $C_{1-4}$ alkyl, $C_{1-4}$ alkylcarbonyl, $C_{1-4}$ alkoxycarbonyl, cyano or phenyl; or $R^1$ and $R^2$ join together to form a cyclopentyl or cyclohexyl ring to which is optionally fused a benzene ring.

The invention is illustrated by the compounds listed in Table I which follows. The compounds have the formula (I.1) in which the values of $R^1$, $R^2$ and Y are given in the Table. Throughout the Table, the oximinoacetate group has the (E)-configuration except where otherwise indicated.

TABLE I

| COMPOUND NO. | $R^1$ | $R^2$ | Y |
|---|---|---|---|
| 1 | 2-CH$_3$O—C$_6$H$_4$ | H | H |
| 2 | 3-CH$_3$O—C$_6$H$_4$ | H | H |
| 3 | 4-CH$_3$O—C$_6$H$_4$ | H | H |
| 4 | 2-CH$_3$—C$_6$H$_4$ | H | H |
| 5 | 3-CH$_3$—C$_6$H$_4$ | H | H |
| 6 | 4-CH$_3$—C$_6$H$_4$ | H | H |
| 7 | 2-F—C$_6$H$_4$ | H | H |
| 8 | 3-F—C$_6$H$_4$ | H | H |
| 9 | 4-F—C$_6$H$_4$ | H | H |
| 10 | 2-Cl—C$_6$H$_4$ | H | H |
| 11 | 3-Cl—C$_6$H$_4$ | H | H |
| 12 | 4-Cl—C$_6$H$_4$ | H | H |
| 13 | 2-Br—C$_6$H$_4$ | H | H |
| 14 | 3-Br—C$_6$H$_4$ | H | H |
| 15 | 4-Br—C$_6$H$_4$ | H | H |
| 16 | 2-NO$_2$—C$_6$H$_4$ | H | H |
| 17 | 3-NO$_2$—C$_6$H$_4$ | H | H |
| 18 | 4-NO$_2$—C$_6$H$_4$ | H | H |
| 19 | 2-CF$_3$—C$_6$H$_4$ | H | H |
| 20 | 3-CF$_3$—C$_6$H$_4$ | H | H |
| 21 | 4-CF$_3$—C$_6$H$_4$ | H | H |
| 22 | C$_6$H$_5$ | H | H |

TABLE I-continued

| COMPOUND NO. | R$^1$ | R$^2$ | Y |
|---|---|---|---|
| 23 | C$_6$H$_5$ | CH$_3$ | H |
| 24 | C$_6$H$_5$ | C$_6$H$_5$ | H |
| 25 | 2-C$_6$H$_5$—C$_6$H$_4$ | H | H |
| 26 | 3-C$_6$H$_5$—C$_6$H$_4$ | H | H |
| 27 | 4-C$_6$H$_5$—C$_6$H$_4$ | H | H |
| 28 | 2-(C$_6$H$_5$CH$_2$O)—C$_6$H$_4$ | H | H |
| 29 | 3-(C$_6$H$_5$CH$_2$O)—C$_6$H$_4$ | H | H |
| 30 | 4-(C$_6$H$_5$CH$_2$O)—C$_6$H$_4$ | H | H |
| 31 | 2-cyano-C$_6$H$_4$ | H | H |
| 32 | 3-cyano-C$_6$H$_4$ | H | H |
| 33 | 4-cyano-C$_6$H$_4$ | H | H |
| 34 | 2-CF$_3$O—C$_6$H$_4$ | H | H |
| 35 | 3-CF$_3$O—C$_6$H$_4$ | H | H |
| 36 | 4-CF$_3$O—C$_6$H$_4$ | H | H |
| 37 | pyrid-2-yl | H | H |
| 38 | pyrid-3-yl | H | H |
| 39 | pyrid-4-yl | H | H |
| 40 | pyrid-2-yl | CH$_3$ | H |
| 41 | pyrid-2-yl | cyano | H |
| 42 | pyrid-2-yl | CO$_2$C$_2$H$_5$ | H |
| 43 | pyrid-2-yl | CO$_2$CH$_3$ | H |
| 44 | pyrimidin-2-yl | H | H |
| 45 | pyrimidin-4-yl | H | H |
| 46 | thien-2-yl | H | H |
| 47 | thien-2-yl | CH$_3$ | H |
| 48 | 5-Cl-thien-2-yl | H | H |
| 49 | CO$_2$C$_2$H$_5$ | CO$_2$C$_2$H$_5$ | H |
| 50 | CO$_2$CH$_3$ | CO$_2$CH$_3$ | H |
| 51 | COCH$_3$ | COCH$_3$ | H |
| 52 | cyano | cyano | H |
| 53 | 0 | 0 | H |
| 54 | 0 | 0 | H |
| 55 | 0 | 0 | H |
| 56 | tert-C$_4$H$_9$ | H | H |
| 57 | C$_6$H$_5$CH$_2$ | H | H |
| 58 | 2,4-di-Cl—C$_6$H$_3$ | H | H |
| 59 | 2,4-di-F—C$_6$H$_3$ | H | H |
| 60 | 3,5-di-CH$_3$—C$_6$H$_3$ | H | H |
| 61 | 3,5-di-CH$_3$O—C$_6$H$_3$ | H | H |
| 62A* | pyrazin-2-yl | CH$_3$ | H |
| 62B* | pyrazin-2-yl | CH$_3$ | H |
| 63 | 6-CH$_3$-pyrid-3-yl | CH$_3$ | H |
| 64 | pyrid-2-yl | C$_2$H$_5$ | H |
| 65 | pyrid-3-yl | CH$_3$ | H |
| 66 | pyrimidin-5-yl | iso-C$_3$H$_7$ | H |
| 67 | iso-C$_3$H$_7$ | pyrimidin-5-yl | H |
| 68 | pyrid-4-yl | CH$_3$ | H |
| 69 | 6-Cl-pyrid-2-yl | CH$_3$ | H |
| 70 | 5-Cl-pyrid-2-yl | CH$_3$ | H |
| 71 | 4-Cl-pyrid-2-yl | CH$_3$ | H |
| 72 | 3-Cl-pyrid-2-yl | CH$_3$ | H |
| 73 | 6-cyano-pyrid-2-yl | CH$_3$ | H |
| 74 | 5-cyano-pyrid-2-yl | CH$_3$ | H |
| 75 | 4-cyano-pyrid-2-yl | CH$_3$ | H |
| 76 | 3-cyano-pyrid-2-yl | CH$_3$ | H |
| 77 | 6-Br-pyrid-2-yl | CH$_3$ | H |
| 78 | 5-Br-pyrid-2-yl | CH$_3$ | H |
| 79 | 4-Br-pyrid-2-yl | CH$_3$ | H |
| 80 | 3-Br-pyrid-2-yl | CH$_3$ | H |
| 81 | 6-CH$_3$-pyrid-2-yl | CH$_3$ | H |
| 82 | 5-CH$_3$-pyrid-2-yl | CH$_3$ | H |
| 83 | 4-CH$_3$-pyrid-2-yl | CH$_3$ | H |
| 84 | 3-CH$_3$-pyrid-2-yl | CH$_3$ | H |
| 85 | 6-F-pyrid-2-yl | CH$_3$ | H |
| 86 | 5-F-pyrid-2-yl | CH$_3$ | H |
| 87 | 4-F-pyrid-2-yl | CH$_3$ | H |
| 88 | 3-F-pyrid-2-yl | CH$_3$ | H |
| 89 | 3-CH$_3$-pyrazin-2-yl | CH$_3$ | H |
| 90 | 3-C$_2$H$_5$-pyrazin-2-yl | CH$_3$ | H |
| 91 | 3-Cl-pyrazin-2-yl | CH$_3$ | H |
| 92 | 3-CH$_3$O-pyrazin-2-yl | CH$_3$ | H |
| 93 | 5-CO$_2$CH$_3$-pyrazin-2-yl | CH$_3$ | H |
| 94 | 5-CO$_2$C$_2$H$_5$-pyrazin-2-yl | CH$_3$ | H |
| 95 | 3-cyano-pyrazin-2-yl | CH$_3$ | H |
| 96 | pyrimidin-4-yl | CH$_3$ | H |
| 97 | 2-Cl-pyrimidin-4-yl | CH$_3$ | H |
| 98 | 2-CH$_3$O-pyrimidin-4-yl | CH$_3$ | H |
| 99 | 2-CH$_3$-pyrimidin-4-yl | CH$_3$ | H |
| 100 | 2-cyano-pyrimidin-4-yl | CH | H |
| 101 | thiazol-2-yl | CH$_3$ | H |

TABLE I-continued

| COMPOUND NO. | R¹ | R² | Y |
|---|---|---|---|
| 102 | thien-3-yl | $CH_3$ | H |
| 103 | 5-Cl-thien-2-yl | $CH_3$ | H |
| 104 | 5-$CH_3$-thien-2-yl | $CH_3$ | H |
| 105 | 5-Br-thien-2-yl | $CH_3$ | H |
| 106 | 5-cyano-thien-2-yl | $CH_3$ | H |
| 107 | 3-$CH_3$-thien-2-yl | $CH_3$ | H |
| 108 | 2-$CH_3O$—$C_6H_4$ | $CH_3$ | H |
| 109 | 3-$CH_3O$—$C_6H_4$ | $CH_3$ | H |
| 110 | 4-$CH_3O$—$C_6H_4$ | $CH_3$ | H |
| 111 | 2-$CH_3$—$C_6H_4$ | $CH_3$ | H |
| 112 | 3-$CH_3$—$C_6H_4$ | $CH_3$ | H |
| 113 | 4-$CH_3$—$C_6H_4$ | $CH_3$ | H |
| 114 | 2-F—$C_6H_4$ | $CH_3$ | H |
| 115 | 3-F—$C_6H_4$ | $CH_3$ | H |
| 116 | 4-F—$C_6H_4$ | $CH_3$ | H |
| 117 | 2-Cl—$C_6H_4$ | $CH_3$ | H |
| 118 | 3-Cl—$C_6H_4$ | $CH_3$ | H |
| 119 | 4-Cl—$C_6H_4$ | $CH_3$ | H |
| 120 | 2-Br—$C_6H_4$ | $CH_3$ | H |
| 121 | 3-Br—$C_6H_4$ | $CH_3$ | H |
| 122 | 4-Br—$C_6H_4$ | $CH_3$ | H |
| 123 | 2-$NO_2$—$C_6H_4$ | $CH_3$ | H |
| 124 | 3-$NO_2$—$C_6H_4$ | $CH_3$ | H |
| 125 | 4-$NO_2$—$C_6H_4$ | $CH_3$ | H |
| 126 | 2-$CF_3$—$C_6H_4$ | $CH_3$ | H |
| 127A* | 3-$CF_3$—$C_6H_4$ | $CH_3$ | H |
| 127B* | 3-$CF_3$—$C_6H_4$ | $CH_3$ | H |
| 128 | 4-$CF_3$—$C_6H_4$ | $CH_3$ | H |
| 129 | 2-cyano-$C_6H_4$ | $CH_3$ | H |
| 130 | 3-cyano-$C_6H_4$ | $CH_3$ | H |
| 131 | 4-cyano-$C_6H_4$ | $CH_3$ | H |
| 132 | 3,4,5-$(CH_3O)_3$—$C_6H_2$ | $CH_3$ | H |
| 133 | 3,5-di-F-pyrid-2-yl | $CH_3$ | H |
| 134 | 3,4,5,6-$F_4$-pyrid-2-yl | $CH_3$ | H |
| 135 | 2,6-di-Cl-pyrid-3-yl | $CH_3$ | H |
| 136 | pyridazin-3-yl | $CH_3$ | H |
| 137 | pyridazin-4-yl | $CH_3$ | H |
| 138 | 6-$CH_3$-pyridazin-3-yl | $CH_3$ | H |
| 139 | 4-cyano-quinolin-2-yl | $CH_3$ | H |
| 140 | quinoxalin-2-yl | $CH_3$ | H |
| 141 | $C_6H_5$ | $CH_3$ | 6-F |
| 142 | $C_6H_5$ | $CH_3$ | 6-Cl |
| 143 | 6-$CH_3$-pyrimidin-4-yl | $CH_3$ | H |
| 144 | 4-$CH_3$-pyrimidin-5-yl | $CH_3$ | H |
| 145 | 4-$CH_3$-pyrimidin-2-yl | $CH_3$ | H |
| 146 | 4,6-di-$CH_3$-pyrimidin-2-yl | $CH_3$ | H |
| 147 | 2,6-di-$CH_3$-pyrimidin-4-yl | $CH_3$ | H |
| 148 | 2,4-di-$CH_3$-pyrimidin-5-yl | $CH_3$ | H |
| 149 | 6-Cl-pyrimidin-4-yl | $CH_3$ | H |
| 150 | 6-$CH_3O$-pyrimidin-4-yl | $CH_3$ | H |
| 151 | 4,6-di-$CH_3O$-pyrimidin-2-yl | $CH_3$ | H |
| 152 | 0 | 0 | H |
| 153 | 0 | 0 | H |
| 154 | pyrid-2-yl, N-oxide | $CH_3$ | H |
| 155 | 5-$C_2H_5$-pyrid-2-yl | $CH_3$ | H |
| 156 | $CH_3CO$ | $CH_3$ | H |
| 157 | $C_6H_5CO$ | $CH_3$ | H |
| 158 | N—$CH_3$-pyrrol-2-yl | $CH_3$ | H |
| 159 | 4-Cl-quinolin-2-yl | $CH_3$ | H |
| 160 | 2,4-di-Cl—$C_6H_3$ | 1,2,4-triazol-l-yl-$CH_2$ | H |
| 161 | 2,4-di-Cl—$C_6H_3$ | pyrid-3-yl-$CH_2$ | H |
| 162 | 4-di-$CH_3$-thiazol-5-yl | $CH_3$ | H |
| 163 | furan-2-yl | $CH_3$ | H |
| 164 | 2,4-di-$CH_3$-furan-3-yl | $CH_3$ | H |
| 165 | pyrid-2-yl | pyrid-2-yl | H |
| 166 | 6-$C_6H_5$-pyrimidin-4-yl | $CH_3$ | H |
| 167 | 4-cyano-pyrid-3-yl | $CH_3$ | H |
| 168 | 1,2,4-triazin-5-yl | $CH_3$ | H |
| 169 | 3-$CH_3$-1,2,4-triazin-5-yl | $CH_3$ | H |
| 170 | 3-$C_6H_5$-1,2,4-triazin-5-yl | $CH_3$ | H |
| 171 | 3-$SCH_3$-1,2,4-triazin-5-yl | $CH_3$ | H |
| 172 | 3-$CH_3O$-1,2,4-triazin-5-yl | $CH_3$ | H |
| 173 | 5-$CONH_2$-pyrazin-2-yl | $CH_3$ | H |
| 174 | 5-cyano-pyrazin-2-yl | $CH_3$ | H |
| 175 | 5,6-di-$CH_3$-pyrazin-2-yl | $CH_3$ | H |
| 176 | 3,5-di-$CH_3$-pyrazin-2-yl | $CH_3$ | H |
| 177 | 3,6-di-$CH_3$-pyrazin-2-yl | $CH_3$ | H |
| 178 | 5-$CH_3$-pyrazin-2-yl | $CH_3$ | H |

TABLE I-continued

| COMPOUND NO. | R¹ | R² | Y |
|---|---|---|---|
| 179 | 6-CH₃-pyrazin-2-yl | CH₃ | H |
| 180 | 5-Cl-pyrazin-2-yl | CH₃ | H |
| 181 | 6-Cl-pyrazin-2-yl | CH₃ | H |
| 182 | 5,6-dicyano-pyrazin-2-yl | CH₃ | H |
| 183 | 4-SO₂CH₃—C₆H₄ | CH₃ | H |
| 184 | 4-NH₂—C₆H₄ | CH₃ | H |
| 185 | 2,4-di-Cl—C₆H₃ | CH₃ | H |
| 186 | 2,4-di-CH₃—C₆H₃ | CH₃ | H |
| 187 | 4-NHCONH₂—C₆H₄ | CH₃ | H |
| 188 | C₆H₅ | cyclopropyl | H |
| 189 | C₆H₅ | Cl | H |
| 190 | 4-C₂H₅O—C₆H₄ | CF₃ | H |
| 191 | C₆H₅ | SCH₃ | H |
| 192 | C₆H₅ | F | H |
| 193 | C₆H₅ | OC₂H₅ | H |
| 194 | C(CH₃)₃ | CH₃ | H |
| 195 | cyclohexyl-CH₂ | CH₃ | H |
| 196 | C₆H₅—CH₂ | CH₃ | H |
| 197 | pyrazin-2-yl-CH₂ | CH₃ | H |
| 198 | (E)-C₆H₅—CH=CH | CH₃ | H |
| 199 | C₆H₅—OCH₂ | CH₃ | H |
| 200 | C₆H₅ | CH₂Cl | H |
| 201 | benzthiazol-2-yl | CH₃ | H |
| 202 | benzoxazol-2-yl | CH₃ | H |
| 203 | pyrazin-2-yl | C₂H₅ | H |
| 204 | 5-CH₃O-pyrazin-2-yl | CH₃ | H |
| 205 | 6-CH₃O-pyrazin-2-yl | CH₃ | H |
| 206 | 6-cyano-pyrazin-2-yl | CH₃ | H |
| 207 | 5-cyano-pyrid-3-yl | CH₃ | H |
| 208 | 6-cyano-pyrid-3-yl | CH₃ | H |
| 209 | 3-cyano-pyrid-4-yl | CH₃ | H |
| 210 | 2-cyano-pyrid-4-yl | CH₃ | H |
| 211 | pyrimidin-5-yl | CH₃ | H |
| 212 | 2-CH₃-pyrimidin-5-yl | CH₃ | H |
| 213 | 3-CH₃O-isoxazol-5-yl | CH₃ | H |
| 214 | 3-Br-isoxazol-5-yl | CH₃ | H |
| 215 | 5-NO₂-thiazol-2-yl | CH₃ | H |
| 216 | 5-CH₃-thiazol-2-yl | CH₃ | H |
| 217 | 4-CH₃-thiazol-5-yl | CH₃ | H |
| 218 | 2-Cl,4-CH₃-thiazol-5-yl | CH₃ | H |
| 219 | 3,5-di-CH₃O-1,2,4-triazin-6-yl | CH₃ | H |
| 220 | 3,6-di-CH₃-pyridazin-4-yl | CH₃ | H |
| 221 | 2-(C₆H₅O)—C₆H₄ | CH₃ | H |
| 222 | 3-(C₆H₅O)—C₆H₄ | CH₃ | H |
| 223 | 4-(C₆H₅O)—C₆H₄ | CH₃ | H |
| 224 | 1,2,4-triazol-l-yl-CH₂ | CH₃ | H |
| 225 | C₆H₅ | OCH₃ | H |
| 226 | OCH₃ | C₆H₅ | H |
| 227 | C₆H₅ | CH₃S(O) | H |
| 228 | C₆H₅ | CH₃S(O)₂ | H |
| 229 | C₆H₅ | N(CH₃)₂ | H |
| 230 | C₆H₅O | CH₃ | H |
| 231 | C₆H₅ | Br | H |
| 232 | C₆H₅ | I | H |
| 233 | C₆H₅ | (CH₃)₂CHS | H |
| 234 | pyrimidin-2-yl | CH₃O | H |
| 235 | pyrazin-2-yl | Cl | H |
| 236 | 3-OC₂H₅-pyrazin-2-yl | CH₃H | H |
| 237 | pyrid-2-yl | SCH₃ | H |
| 238 | pyrid-2-yl | SO₂CH₃ | H |
| 239 | Pyrid-2-yl | SOCH₃ | H |
| 240 | 3,5-di-CH₃-oxaz-ol-4-yl | CH₃ | H |
| 241 | pyrid-2-yl | OCH₃ | H |
| 242 | pyrid-2-yl | SC₂H₃ | H |
| 243 | pyrid-2-yl | OC₆H₅ | H |
| 244 | pyrid-2-yl | OCH₂—C₆H₅ | H |
| 245 | 6-OC₂H₅-pyrimid-in-4-yl | CH₃H | |
| 246 | pyrid-2-yl | NH₂ | H |
| 247 | SCH₃ | pyrid-2-yl | H |
| 248 | 2,4-di-F—C₆H₃ | CH₃ | H |
| 249 | 2,4-di-OCH₃—C₆H₃ | CH₃ | H |
| 250 | 5-CH₃-pyrimidin-2-yl | CH₃ | H |
| 251 | SO₂CH₃ | pyrid-2-yl | H |
| 252 | pyrid-3-yl | SCH₃ | H |
| 253 | pyrid-3-yl | OCH₃ | H |
| 254 | 6-CF₃-pyrid-2-yl | CH₃ | H |
| 255 | 3-CF₃,4-F—C₆H₃ | CH₃ | H |
| 256 | 6-CF₃-pyrimidin-4-yl | CH₃ | H |
| 257 | 3,5-di-F—C₆H₃ | CH₃ | H |
| 258 | 2-CH₃S-pyrimidin-4-yl | CH₃ | H |

TABLE I-continued

| COMPOUND NO. | R$^1$ | R$^2$ | Y |
|---|---|---|---|
| 259 | 2-CF$_3$-pyrimidin-4-yl | CH$_3$ | H |
| 260 | 4-CF$_3$-pyrid-2-yl | CH$_3$ | H |
| 261 | 2-phenyl-thiazol-4-yl | CH$_3$ | H |
| 262 | 3-NH$_2$C(O)—C$_6$H$_4$ | CH$_3$ | H |
| 263 | 4-CF$_3$-pyrimidin-2-yl | CH$_3$ | H |
| 264 | 3,5-di-CF$_3$—C$_6$H$_3$ | CH$_3$ | H |
| 265 | 2-(2-CN-C$_6$H$_4$-O-)-pyrimidin-4-yl | CH$_3$ | H |
| 266 | 3-n-C$_3$H$_7$O—C$_6$H$_4$ | CH$_3$ | H |
| 267 | 2-CH(CH$_3$)$_2$—O-pyrimidin-4-yl | CH$_3$ | H |
| 268 | 6-CF$_3$-pyrazin-2-yl | CH$_3$ | H |
| 269 | 4-C$_2$H$_5$O-pyrimidin-2-yl | CH$_3$ | H |
| 270 | 6-C$_2$F$_5$-pyrimidin-4-yl | CH$_3$ | H |
| 271 | 3-CF$_3$O—C$_6$H$_4$ | CH$_3$ | H |
| 272 | 4-CH$_3$O-pyrid-2-yl | CH$_3$ | H |
| 273 | 2-propargyloxy-pyrimidin-4-yl | CH$_3$ | H |
| 274 | 2-C$_2$H$_5$O-pyrimidin-4-yl | CH$_3$ | H |
| 275 | 2-allyloxy-pyrimidin-4-yl | CH$_3$ | H |
| 276 | 3-CH$_3$O-pyridazin-6-yl | CH$_3$ | H |
| 277 | 3-C$_2$H$_5$O-pyridazin-6-yl | CH$_3$ | H |
| 278 | 3-allyloxy-C$_6$H$_4$ | CH$_3$ | H |
| 279 | 4-CH$_3$S-pyrimidin-2-yl | CH$_3$ | H |
| 280 | 4-CH$_3$O-pyrimidin-2-yl | CH$_3$ | H |
| 281 | 3-CF$_3$—C$_6$H$_4$ | SCH$_3$ | H |
| 282 | 3-CF$_3$—C$_6$H$_4$ | CF$_3$ | H |
| 283 | 3-CF$_3$—C$_6$H$_4$ | C$_2$H$_5$ | H |
| 284 | 3-CF$_3$—C$_6$H$_4$ | NH$_2$ | H |
| 285 | 3-CF$_3$—C$_6$H$_4$ | Imidazolyl | H |
| 286 | 3-CF$_3$—C$_6$H$_4$ | N(CH$_3$)$_2$ | H |
| 287 | 3-CF$_3$—C$_6$H$_4$ | NHCH$_3$ | H |
| 288 | PO(OC$_2$H$_5$)$_2$ | CH$_3$ | H |
| 289 | PO(OC$_2$H$_5$)$_2$ | C$_6$H$_5$ | H |
| 290 | 4-CH$_3$O-6-(CO$_2$CH$_3$)-pyrimidin-2-yl | CH$_3$ | H |
| 291 | pyrrol-2-yl | CH$_3$ | H |
| 292 | CH$_3$ | pyrrol-2-yl | H |
| 293 | 5-CF$_3$-pyrid-3-yl | CH$_3$ | H |
| 294 | 3-(pyrimidinyloxy)-C$_6$H$_4$ | CH$_3$ | H |
| 295 | 3-propargyloxy-C$_6$H$_4$ | CH$_3$ | H |
| 296 | CH$_3$ | H | N |
| 297 | 5-(2,4-difluorophenyl)-furan-2-yl | CH$_3$ | H |
| 298 | CH$_3$ | 5-(2,4-difluorophenyl)-furan-2-yl | H |
| 299 | C$_2$H$_5$O | CH$_3$ | H |
| 300 | 4-tert-butyl-C$_6$H$_4$ | CH$_3$ | H |
| 301 | 4-propargyloxy-pyrimidin-2-yl | CH$_3$ | H |
| 302 | 2-C$_2$H$_5$O—C$_6$H$_4$ | CH$_3$ | H |
| 303 | 4-C$_2$H$_5$—C$_6$H$_4$ | CH$_3$ | H |
| 304 | 3-C$_2$H$_5$O—C$_6$H$_4$ | CH$_3$ | H |
| 305 | CH$_3$S | CH$_3$ | H |
| 306 | CH$_3$SO$_2$ | CH$_3$ | H |
| 307 | 0 | 0 | H |
| 308 | 4-n-C$_3$H$_7$O-pyrimidin-2-yl | CH$_3$ | H |
| 309 | 3-n-hexyloxy-C$_6$H$_4$ | CH$_3$ | H |
| 310 | 4-n-butyloxy-pyrimidin-2-yl | CH$_3$ | H |
| 311 | benzothiophen-3-yl | CH$_3$ | H |
| 312 | 3-[(CH$_3$)$_2$C=CHCH$_2$O]-C$_6$H$_4$ | CH$_3$ | H |
| 313 | 2,4-di-CH$_3$O-pyrimidin-6-yl | CH$_3$ | H |
| 314 | 3-CF$_3$—C$_6$H$_4$ | 1,2,4-triazol-l-yl | H |
| 315 | 3-CH$_3$S-pyrazin-2-yl | CH$_3$ | H |
| 316 | 3-N(CH$_3$)$_2$—C$_6$H$_4$ | CH$_3$ | H |
| 317 | 3-CF$_3$—C$_6$H$_4$ | Cl | H |
| 318 | 0 | 0 | H |
| 319 | benzofuran-2-yl | CH$_3$ | H |
| 320 | 2-CH$_3$S(O)-pyrimidin-4-yl | CH$_3$ | H |
| 321 | 3-NH$_2$C(S)-C$_6$H$_4$ | CH$_3$ | H |
| 322 | 4-NH$_2$C(S)-pyrid-2-yl | CH$_3$ | H |
| 323 | 3-(CH$_3$OCH$_2$CH$_2$OCH$_2$O)—C$_6$H$_4$ | CH$_3$ | H |
| 324 | 3-(cyanomethoxy)-C$_6$H$_4$ | CH$_3$ | H |
| 325 | 0 | 0 | H |
| 326 | 3-(F$_2$HC—O—)—C$_6$H$_4$ | CH$_3$ | H |
| 327 | 6-C$_2$H$_5$O-pyrazin-2-yl | CH$_3$ | H |

Key
*Compounds 62A, 62B, 127A and 127B are the isomers identified in Table II below.
0 Groups R$^1$ and R$^2$ join to form a ring as shown under "Chemical Formulae" later.

TABLE II

MELTING POINTS AND OXIMINO-ACETATE ISOMER
Table II shows melting points for certain compounds described in Table I and whether the oximino-acetate group has the (E)- or (Z)-configuration.

| Compound No | Isomer (E) or (Z) | Melting Point °C. |
|---|---|---|
| 62A | Z | Oil |
| 62B | E | 117–120 |
| 127A | Z | Oil |
| 127B | E | Oil |
| 130 | E | 97 |
| 260 | E | 94.4–96.6 |
| 269 | E | 105 |
| 321 | E | 126–8 |

TABLE III

SELECTED PROTON NMR DATA
Table III shows selected proton NMR data for certain compounds described in Table I. Chemical shifts are measured in ppm from tetramethylsilane, and deuterochloroform was used as solvent throughout. The operating frequency of the NMR spectrometer was 270 MHz unless otherwise specified. The following abbreviations are used:

br = broad        t = triplet
s = singlet       q = quartet
d = doublet       m = multiplet

| Compound No | NMR Data |
|---|---|
| 62A | 2.39(3H, s), 3.91(3H, s), 4.06(3H, s), 5.56(2H, s) 7.3–7.6(4H, m), 8.51(2H, m), 9.15(1H, m)ppm. |
| 62B | 2.28(3H, s), 3.86(3H, s), 4.05(3H, s), 5.19(2H, s), 7.1–7.6(4H, m), 8.50(2H, m), 9.10(1H, m)ppm. |
| 127A | 2.33(3H, s), 3.88(3H, s), 4.02(3H, s), 5.50(2H, s), 7.3–7.9(8H, m)ppm. |
| 127B | 2.21(3H, s), 3.82(3H, s), 4.03(3H, s), 5.15(2H, s), 7.1–7.9(8H, m)ppm. |

The compounds of the invention having the formula (I) can be prepared by the routes shown in Scheme I. Throughout Scheme I the terms Y, $R^1$ and $R^2$ are as defined above, L is a leaving group such as halogen (chlorine, bromine or iodine), and Q is a halogen (chlorine, bromine or iodine). Each reaction is performed in a suitable solvent or without a solvent and at a suitable temperature.

Thus compounds of the invention having the formula (I) can be prepared by treating ketoesters of formula (II) with methoxylamine (or a salt of methoxylamine).

Alternatively, compounds of the invention having the formula (I) can be prepared by methylation of oximes of formula (VII) using a methylating agent such as a methyl halide (methyl iodide, methyl bromide or methyl chloride) or dimethylsulphate, usually in the presence of a base such as sodium methoxide or potassium carbonate (see, for example, H S Anker and H T Clarke, *Organic Synthesis*, Collective Vol. 3, 172). Diazomethane may also be used for this O-methylation.

Alternatively, compounds of the invention of formula (I) may be prepared by reaction between oximes of formula (XIII) and oxime ethers of formula (VIII), generally in the presence of a base. One way of performing this reaction is to treat the oxime (XIII) with the base (such as sodium hydride or sodium methoxide) in a solvent (such as N,N-dimethylformamide or tetrahydrofuran) and then to add the oxime ether (VIII) to the resulting oxime anion.

Ketoesters of the formula (II) may be prepared by treating methyl 3-methoxypropenoates of the formula (III) with an oxidising agent such as potassium permanganate or ozone. Methyl 3-methoxypropenoates of the formula (III) can be prepared using the methods described in EP-A-0370629. Alternatively ketoesters of the formula (II) may be prepared by treating a ketoester of formula (IV) with an oxime of formula (XIII) and a suitable base such as silver carbonate in a suitable solvent such as hexane or toluene.

Other methods for the preparation of the ketoester of formula (II) include the oxidation of phenylacetates of formula (V) with a suitable oxidising agent such as selenium dioxide; and treatment of a phenyl halide of formula (VI) with a metalating species (for example butyl-lithium or magnesium) and reacting the product with an oxalate species of formula $GCOCO_2CH_3$, wherein G is a methoxy group, a chlorine atom or an imidazole ring (see, for example, J S Nimitz and H S Mosher, *Journal of Organic Chemistry* 1981, 46, 211–213).

Ketoesters of formula (IV) are described in EP-A-0363818 and can be prepared by the halogenation (especially chlorination or bromination) of ketoesters of formula (X).

Oximes of formula (VII) can be prepared by nitrosation of phenylacetates of formula (V) using either nitrous acid or an ester of nitrous acid in the presence of a base such as sodium methoxide (see, for example, O. Touster, *Organic Reactions*, 1953, 7, 327, particularly page 342 and S Kukolja, S E Draheim, B J Graves, D C Hunden, J L Pfeil, R D G Cooper, J L Ott, and F T Counter, *J. Med. Chem.*, 1985, 28, 1896). Alternatively, oximes of formula (VII) can be prepared by treating ketoesters of formula (II) with hydroxylamine (or a salt of hydroxylamine).

Other methods for the preparation of oximes (VII) have been reported in the chemical literature (see, for example, T Shimizu, Y Hayashi and K Teramura, *Bull. Chem. Soc. Jpn.*, 1985, 58, 2519; G W Shaffer, *Can. J. Chem.*, 1970, 48, 1948).

Phenylacetates of formula (V), oxime ethers of formula (VI) and oximes of formula (XIII) can be prepared by standard procedures described in the chemical literature.

Oxime ethers of the formula (VIII) are described in EP-A-0254426. They are prepared by halogenation (especially chlorination or bromination) of oxime ethers of formula (IX). Oxime ethers of formula (IX) can be prepared from ketoesters of formula (X) by treatment with methoxylamine (or a salt of methoxylamine). Oxime ethers of formula (IX) can be prepared by methylation of oximes of formula (XI) using methods described previously. Oximes of formula (XI) may be prepared either by treatment ketoesters of formula (X) with hydroxylamine (or a salt of hydroxylamine) or by nitrosation of a phenylacetate of formula (XII) using methods described for the preparation of oximes of formula (VII) from phenylacetates of formula (V).

The compounds are active fungicides and may be used to control one or more of the following pathogens: *Pyricularia oryzae* on rice; *Puccinia recondita*, *Puccinia striiformis* and other rusts on wheat, *Puccinia hordei*, *Puccinia striiformis* and other rusts on barley, and rusts on other hosts e.g. coffee, pears, apples, peanuts, vegetables and ornamental plants; *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; *Helminthosporium* spp., *Rhynchosporium* spp., *Septoria* spp., *Pyrenophora* spp., *Pseudo-*

*cercosporella herpotrichoides* and *Gaeumannomyces graminis* on cereals; *Cercospora arachidicola* and *Cercosporidium personata* on peanuts and other *Cercospora* species on other hosts, for example, sugar beet, bananas, soya beans and rice; *Botrytis cinerea* (grey mould) on tomatoes, strawberries, vegetables, vines and other hosts; *Alternaria* spp. on vegetables (e.g. cucumber), oil-seed rape, apples, tomatoes and other hosts; *Venturia inaequalis* (scab) on apples; *Plasmopara viticola* on vines; other downy mildews such as *Bremia lactucae* on lettuce, *Peronospora* spp. on soybeans, tobacco, onions and hosts, *Pseudoperonospora humuli* on hops and *Pseudoperonospora cubensis* on cucurbits; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and other *Rhizoctonia* species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including *Fusarium* spp., *Septoria* spp., *Tilletia* spp., (bunt, a seed-borne disease of wheat), *Ustilago* spp. and *Helminthosporium* spp. on cereals, *Rhizoctonia solani* on cotton and *Pricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition.

The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl-or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-l-ylmethyl)butyronitrile, (Z)-N-but-2-enyloxymethyl-2-chloro-2′,6′-diethylacetanilide, 1-(2-cyano-2-methoxyiminoacetyl)-3-ethyl urea, 3-(2,-dichlorophenyl)-2-(1H-1,2,4-triazol-1-yl)quinazolin-(3H)-one, 4-bromo-2-cyano-N,N-dimethyl-6-trifluoro-methylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1′-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(-methyl-thioethlideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetraconazole, thiabendazole, thicyofen, thiophanate-methyl, thiram, tolclofos-methyl, triacetate salt of 1,1′-iminodi(octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. Throughout the Examples, the term 'ether'refers to diethyl ether, magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. Where shown, infrared and NMR data are selective; no attempt is made to list every absorption in all cases. $^1H$ NMR spectra were recorded using $CDCl_3$-solutions unless otherwise stated. The following abbreviations are used throughout:

| | |
|---|---|
| THF = tetrahydrofuran | s = singlet |
| DMF = N,N-dimethylformamide | d = doublet |
| NMR = nuclear magnetic resonance | t = triplet |
| IR = infrared | m = multiplet |
| m.p. = melting point | br = broad |
| HPLC = high performance liquid chromatography. | |

EXAMPLE 1

This Example illustrates the preparation of two stereoisomers of methyl 2-[E-methyl(3-trifluoromethyl-phenyl)oximinomethyl]phenyl (O-methyloximino)acetate (Compounds No. 127A and 127B of Table I).

A solution of (E,E)-methyl 3-methoxy-2-[2-(methyl(3-trifluoromethyl-phenyl)oximinomethyl)phenyl]-propenoate (2.0 g as prepared in EP-A-0370629) in dichloromethane (20 ml) was added to potassium permanganate (0.93g) in water (20 ml) containing tetra-n-hexyl-ammonium hydrogensulphate (0.1 g). After stirring for 2 hours, the reaction mixture was poured into sodium metabisulphite solution (40 mls of a 10% aqueous solution) and extracted with dichloromethane. The combined organic extracts were dried, concentrated and chromatographed using a mixture of ether and hexane (1:1) as the eluant to give (E)-methyl 2-[methyl(3-trifluoromethylphenyl)oximinomethyl]phenyl-glyoxalate (1.01 g, 54% yield) as a clear oil; $^1H$ NMR : δ2.31(3H,s), 3.92(3H,s), 5.60(2H,s), 7.4–7.9(8H,m) ppm; IR maxima (film): 1740, 1686 $cm^{-1}$.

A solution of (E)-methyl 2-[methyl(3-trifluoromethylphenyl)oximinomethyl]phenylglyoxalate (0.5 g), methoxylamine hydrochloride (0.35 g) and sodium acetate (0.5 g) in methanol (50 ml) was refluxed for 6 hours. The methanol was evaporated off and the residue was partioned between water and ether. The aqueous phase was re-extracted with ether and the combined ether extracts were dried and concentrated to give an oil. Separation by HPLC using a mixture of ether and hexane (1:1) as eluant gave the two isomeric title compounds:

(A) the less polar compound (0.262 g, 30% yield) as a clear oil; $^1H$ NMR given in Table III; mass spectrum: $MH^+$ 409.

(B) as the more polar compound (0.389 g, 45% yield) as a clear oil. $^1H$ NMR given in Table III; mass spectrum: $MH^+$ 409.

EXAMPLE 2

This Example illustrates the preparation of (E)-methyl 2-[(E)-methyl-(3-cyanophenyl)oximinomethyl]-phenyl(O-methyloximino)acetate (Compound No. 130 of Table I).

3-Cyano-acetophenone oxime (0.39 g) was added to a stirred suspension of sodium hydride (0.06 g) in DMF (20 ml). After 3 hours, the reaction mixture was cooled to 0° C. and a solution of (E)-methyl 2-(bromomethyl)-phenylgloxylate-O-methyloxime (0.7 g, prepared as described in EP-A-0363818) in DMF (10 ml) was added dropwise. After 16 hours the reaction mixture was poured into water and extracted with ether. The organic extracts were washed with brine, dried, concentrated and chromatographed using ether:hexane (7:3) as the eluant to give the title compound (0.45 g, 47% yield) as a white solid, m.p. 97° C.; IR maxima (nujol mull): 2232, 1740 $cm^{-1}$; NMR (270 MHz): δ2.19(3H,s), 3.83(3H,s), 5.13(2H,s), 7.1–8.0(3H,m) ppm; mass spectrum: $MH^+$ 366.

The following are examples of compositions suitable for agricultural and horticultural purposes which can be formulated from the compounds of invention. Such compositions form another aspect of the invention. Percentages are by weight.

EXAMPLE 3

An emulsifiable concentrate is made up by mixing and stirring the ingredients until all are dissolved.

| | |
|---|---|
| Compound No. 62B | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 4

The active ingredient is dissolved in methylene dichloride and the resultant liquid sprayed on to the granules of attapulgite clay. The solvent is then allowed to evaporate to produce a granular composition.

| | |
|---|---|
| Compound No. 62B | 5% |
| Attapulgite granules | 95% |

EXAMPLE 5

A composition suitable for use as a seed dressing is prepared by grinding and mixing the three ingredients.

| | |
|---|---|
| Compound No. 62B | 50% |
| Mineral oil | 2% |
| China clay | 48% |

EXAMPLE 6

A dustable powder is prepared by grinding and mixing the active ingredient with talc.

| | |
|---|---|
| Compound No. 62B | 5% |
| Talc | 95% |

EXAMPLE 7

A suspension concentrate is prepared by ball milling the ingredients to form an aqueous suspension of the ground mixture with water.

| Compound No. 62B | 40% |
| --- | --- |
| Sodium lignosulphonate | 10% |
| Bentonite clay | 1% |
| Water | 49% |

This formulation can be used as a spray by diluting into water or applied directly to seed.

EXAMPLE 8

A wettable powder formulation is made by mixing together and grinding the ingredients until all are thoroughly mixed.

| Compound No. 62B | 25% |
| --- | --- |
| Sodium lauryl sulphate | 2% |
| Sodium lignosulphonate | 5% |
| Silica | 25% |
| China clay | 43% |

EXAMPLE 9

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease on untreated plants The results are shown in Table IV.

TABLE IV

| COMPOUND NUMBER | PUCCINIA RECONDITA | ERYSIPHE GRAMINIS TRITICI | SEPTORIA NODORUM | PYRICULARIA ORYZAE | VENTURIA INAEQUALIS | PLASMOPARA VITICOLA | PHYTOPHTHORA INFESTANS |
| --- | --- | --- | --- | --- | --- | --- | --- |
| 62A | $0^a$ | $2^a$ | $0^a$ | $0^a$ | $0^a$ | $0^a$ | $0^a$ |
| 62B | $0^a$ | $0^a$ | $0^a$ | $0^a$ | $4^a$ | $0^a$ | $0^a$ |
| 127A | 4 | 3 | 3 | 3 | 4 | 1 | 3 |
| 127B | 4 | 3 | 4 | 4 | 4 | 4 | 3 |
| 130 | 0 | 0 | 3 | 2 | 2 | 3 | 3 |
| 269 | 1 | 3 | 2 | 4 | 4 | 4 | 0 |
| 321 | 4 | 1 | 4 | 4 | 4 | 4 | 4 |

$a$ = 10 ppm Foliar spray only

CHEMICAL FORMULAE (in description)

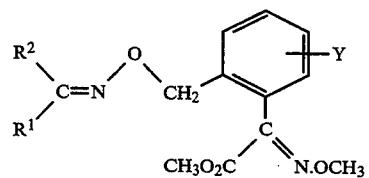

(I)

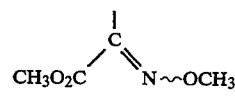

(A)

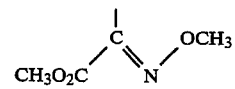

(B)

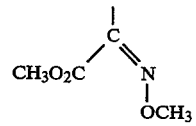

(C)

TABLE I

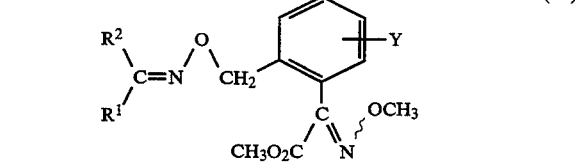

(I.1)

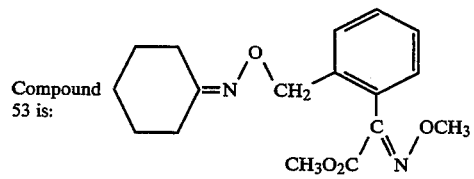

Compound 53 is:

TABLE I-continued
(I.1)
Compound 54 is: [structure]
Compound 55 is: [structure]
Compound 152 is: [structure]
Compound 153 is: [structure]
Compound 307 is: [structure]
Compound 318 is: [structure]
Compound 325 is: [structure]
Scheme I
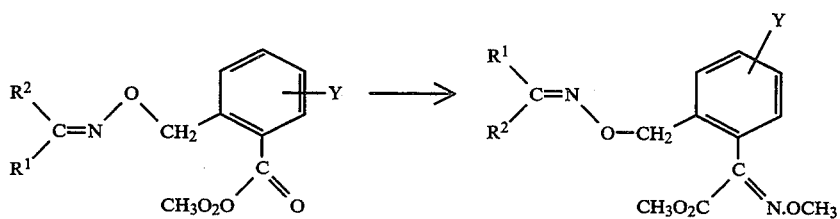

-continued
Scheme I
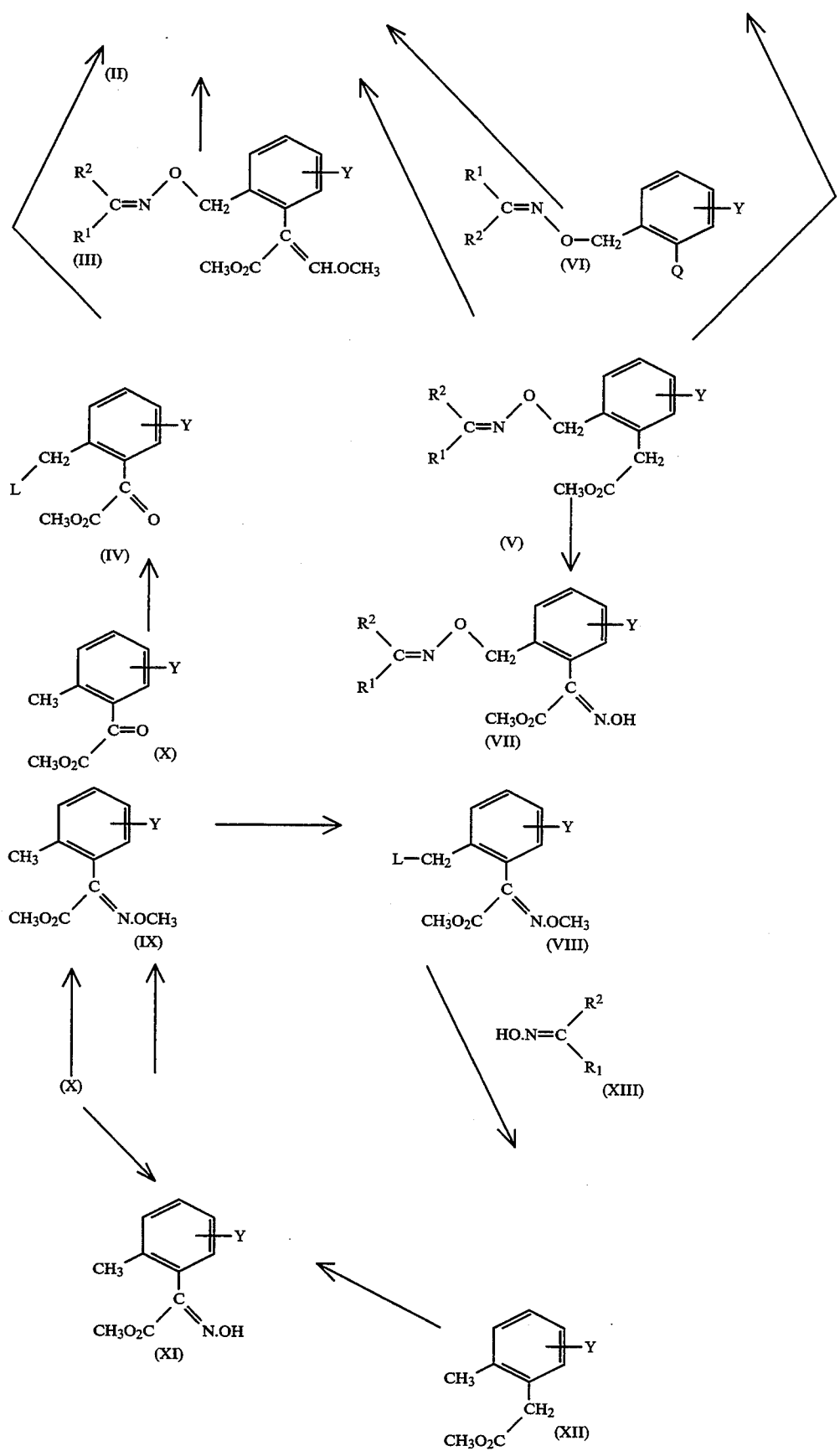

We claim:

1. A compound having the general formula (I):

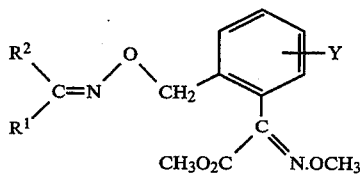

and stereoisomers thereof, wherein Y is hydrogen, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$ is a substituted monocyclic heteroaryl ring having two nitrogen atoms; and $R^2$ is hydrogen, optionally substituted alkyl, optionally substituted cycloalkyl or optionally substituted aralkyl.

2. A compound according to claim 1 wherein Y is hydrogen, halo, hydroxy, methyl, methoxy, halo($C_{1-4}$)alkyl, halo($C_{1-4}$)alkoxy, $C_{1-2}$ alkylcarbonyl, $C_{1-2}$ alkoxycarbonyl, phenoxy, nitro or cyano; $R^1$ is a membered mono-cyclic aromatic heterocycle containing two nitrogen atoms and being substituted with one or more of halo, hydroxy, $C_{1-4}$ alkyl, halo($C_{1-4}$)alkyl, $C_{1-4}$ alkoxy, halo($C_{1-4}$) alkoxy, $C_{1-4}$ alkylcarbonyl, $C_{1-4}$ alkoxycarbonyl, nitro, cyano, phenyl, phenoxy, benzyl or benzyloxy; and $R^2$ is hydrogen, $C_{1-4}$ alkyl, or halo($C_{1-4}$)alkyl.

3. A compound according to claim 1 wherein Y is hydrogen or halo; $R^1$ is pyrimidinyl, pyrazinyl, or pyridazinyl, the foregoing being substituted with one or more of halo, $C_{1-4}$ alkyl, halo($C_{1-4}$)alkyl, $C_{1-4}$ alkoxy, halo($C_{1-4}$)alkoxy, nitro, cyano, phenyl or benzyloxy; and $R^2$ is hydrogen, $C_{1-4}$ alkyl, $C_{1-4}$ alkylcarbonyl, $C_{1-4}$ alkoxycarbonyl, cyano or phenyl.

4. A compound according to claim 1 wherein Y is hydrogen, $R^1$ is 2-, 4- or 5-pyrimidinyl, any of which is substituted with one or more of halo, $C_{1-4}$ alkyl, halo($C_{1-4}$) alkyl, $C_{1-4}$ alkoxy, halo($C_{1-4}$) alkoxy, nitro, cyano, phenyl or benzyloxy; and $R^2$ is methyl.

5. A compound according to claim 1 wherein Y is hydrogen, $R^1$ is 2-pyrimidinyl substituted with one or more of halo, $C_{1-4}$ alkyl, halo($C_{1-4}$)alkyl, $C_{1-4}$ alkoxy, halo($C_{1-4}$)alkoxy, nitro, cyano, phenyl or benzyloxy; and $R^2$ is methyl.

6. A compound according to claim 1 wherein Y is hydrogen, $R^1$ is 4-pyrimidinyl substituted with one or more of halo, $C_{1-4}$ alkyl, halo($C_{1-4}$)alkyl, $C_{1-4}$ alkoxy, halo($C_{1-4}$)alkoxy, nitro, cyano, phenyl or benzyloxy; and $R^2$ is methyl.

7. A compound in accordance with claim 1 wherein $R^1$ is 4-ethoxy pyrimidyl and $R^2$ is methyl.

8. A compound in accordance with claim 7 wherein $R^1$ is 4-ethoxy-pyrimidin-2-yl.

9. A fungicidal composition comprising a fungicidally effective amount of a compound according to claim 1 and a fungicidally acceptable carrier or diluent therefor.

10. A method of combating fungi which comprises applying to plants, to the seeds of plants or to the locus of the plants or seeds, a compound according to claim 1.

* * * * *

Adverse Decisions In Interference

Patent No. 5,346,902, John M. Clough, Christopher R. A. Godfrey, Paul J. DeFraine, FUNGICIDAL DIAZINYL DIOXIME, Interference No. 103,744, final judgment adverse to the patentees rendered February 15, 2001, as to claims 1-10.

*(Official Gazette April 17, 2001)*